United States Patent
Policastro, Jr.

(10) Patent No.: US 7,311,685 B1
(45) Date of Patent: Dec. 25, 2007

(54) FAST DRYING, WATER PERMEABLE PADDING AND IMMOBILIZATION APPARATUS AND METHOD THEREOF

(76) Inventor: Thomas D. Policastro, Jr., 25 Follett Dr., Wrentham, MA (US) 02093

( * ) Notice: Subject to any disclaimer, the term of this patent is extended or adjusted under 35 U.S.C. 154(b) by 155 days.

(21) Appl. No.: 10/770,671

(22) Filed: Feb. 2, 2004

(51) Int. Cl.
    A61F 5/00 (2006.01)
(52) U.S. Cl. ............... 602/3; 602/6; 602/5; 602/41; 2/227
(58) Field of Classification Search ............. 602/3, 602/47, 56, 59, 75–79, 60, 77, 5, 41–46; 428/304.4, 319.9, 95; 604/304; 2/267, 227
See application file for complete search history.

(56) References Cited

U.S. PATENT DOCUMENTS

| | | | | |
|---|---|---|---|---|
| 3,683,921 A | * | 8/1972 | Brooks et al. | 604/366 |
| 3,820,162 A | * | 6/1974 | McGrew | 2/2.11 |
| 4,235,228 A | * | 11/1980 | Gaylord et al. | 602/8 |
| 4,360,015 A | * | 11/1982 | Mayer | 602/47 |
| 4,695,496 A | * | 9/1987 | Lee | 428/95 |
| 4,826,498 A | * | 5/1989 | Koczab | 604/383 |
| 5,016,622 A | * | 5/1991 | Norvell | 602/7 |
| 5,380,260 A | * | 1/1995 | Blott | 602/41 |
| 5,527,265 A | * | 6/1996 | McKeel | 602/6 |
| 5,593,395 A | * | 1/1997 | Martz | 604/304 |
| 5,817,391 A | * | 10/1998 | Rock et al. | 428/86 |
| 5,870,785 A | * | 2/1999 | Hoorens | 5/652.1 |
| 5,941,840 A | * | 8/1999 | Court et al. | 602/47 |
| 5,994,613 A | * | 11/1999 | Cummings et al. | 602/58 |
| 6,083,857 A | * | 7/2000 | Bottger et al. | 442/370 |
| 6,923,219 B2 | * | 8/2005 | Shteiyer | 139/397 |
| 6,967,261 B1 | * | 11/2005 | Soerens et al. | 602/48 |
| 7,043,767 B2 | * | 5/2006 | Jaeger | 2/87 |
| 7,176,343 B2 | * | 2/2007 | Schlussel | 602/41 |

* cited by examiner

*Primary Examiner*—Justine R. Yu
*Assistant Examiner*—Shumaya Ali

(57) ABSTRACT

An immobilization apparatus incorporating a water permeable padding design that channels water away from the wearer and a method of preparing an immobilizing apparatus is described. In human or veterinary applications, the apparatus can be flushed with various solutions for cleansing of the limb beneath while avoiding the accumulation of excess moisture. The apparatus can be immersed in water then dried quickly in the open air. Subject invention allows for effective transfer of moisture away from the skin thereby avoiding skin maceration.

27 Claims, 5 Drawing Sheets

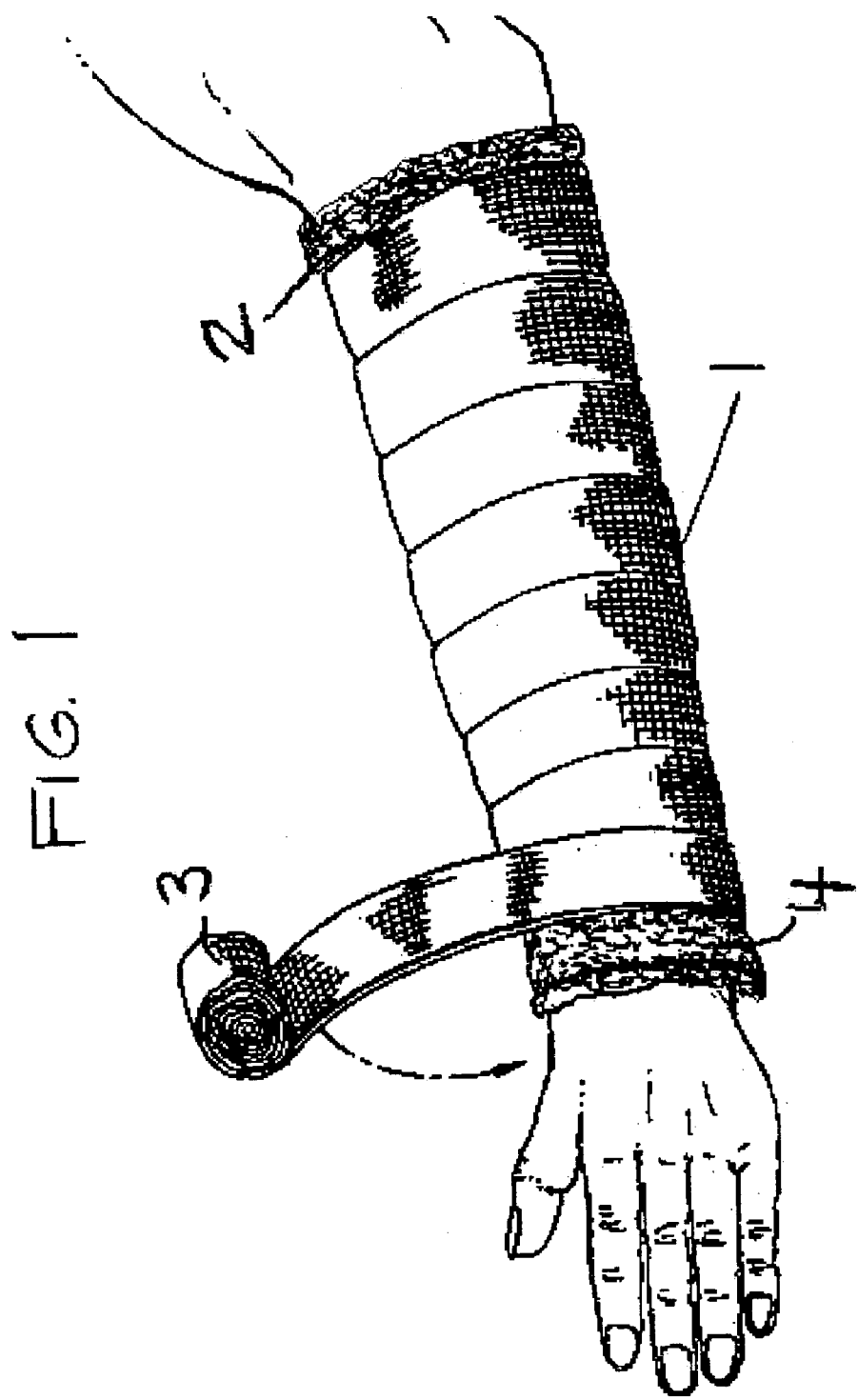

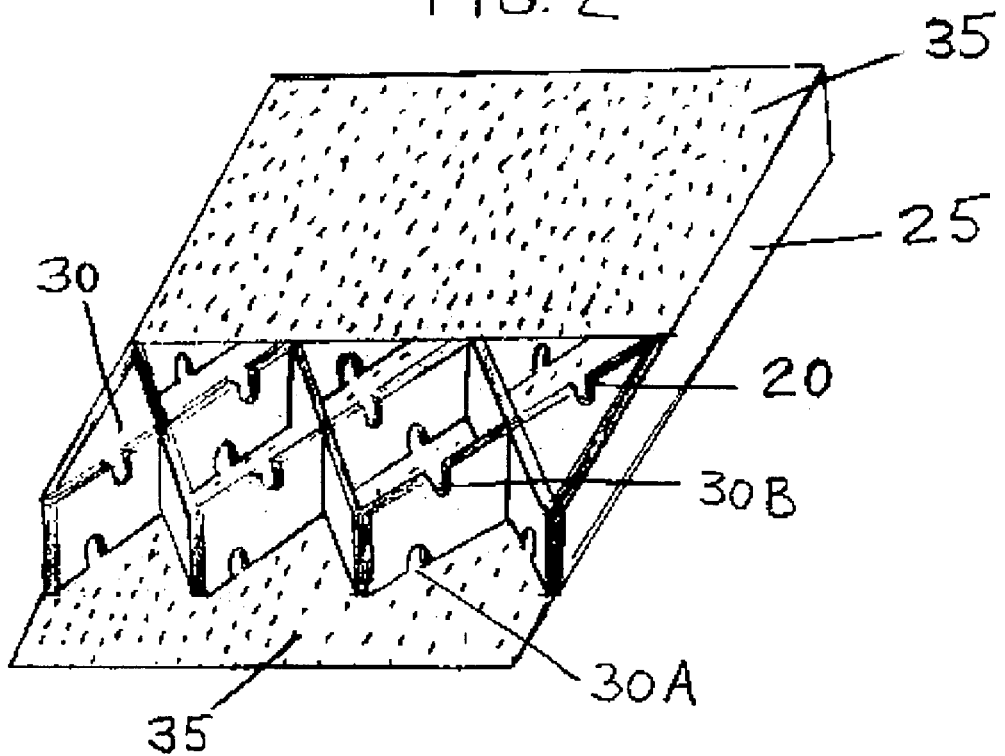
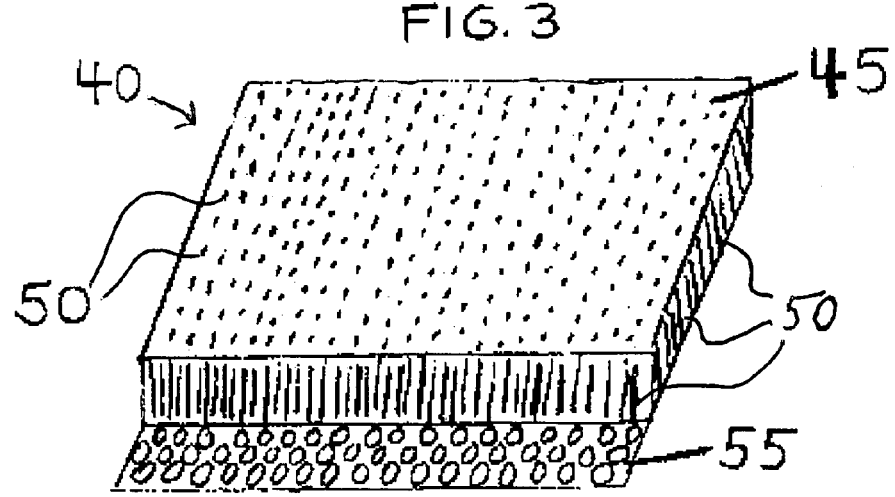

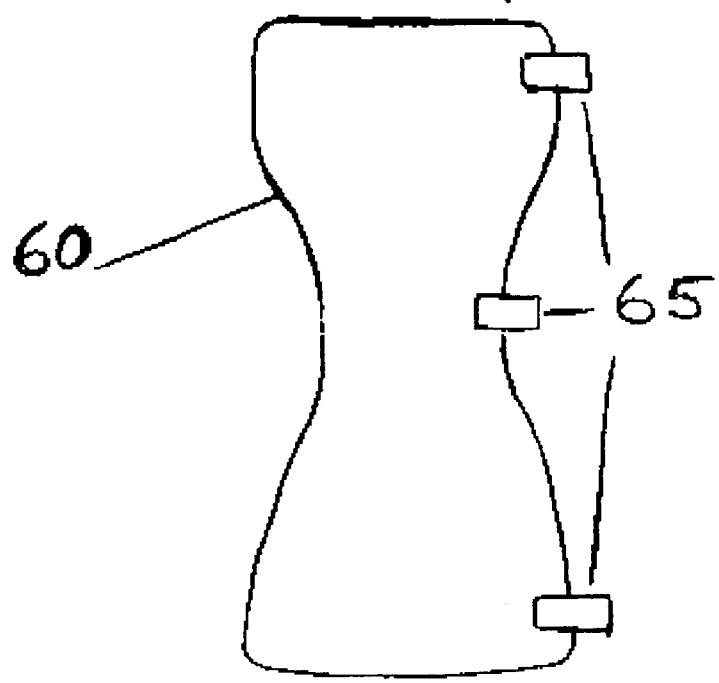
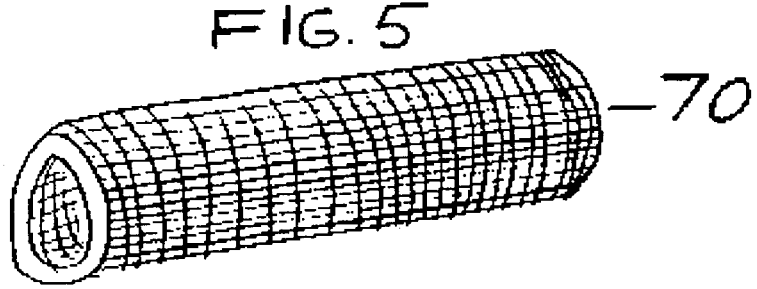

FAST DRYING, WATER PERMEABLE PADDING AND IMMOBILIZATION APPARATUS AND METHOD THEREOF

BACKGROUND OF THE INVENTION

1. Field of the Invention

The present invention relates to fast drying, water permeable padding, which is utilized in any immobilization apparatus, in particular, an apparatus and method is disclosed for casting or immobilizing any part of a human or animal anatomy.

2. Description of Related Art

There are many types of padding materials currently used under rigid casts or other immobilization apparatuses. These traditional padding materials include cotton, rayon, polyester, polypropylene and other types of synthetic materials. In one method of applying a rigid cast, a tube of stockinet is first applied to the limb followed by a layer of padding. An immobilizing material is next applied on top of the padding and consists of either a Plaster of Paris impregnated substrate, a polyurethane-coated substrate or any other type of bracing or splinting material. Traditional cast underpad is supplied in rolls in widths from 2 to 6 inches. The purpose of underpad is to provide cushioning of the limb and to maintain conformity against the limb so as not to form folds or creases against the skin which could result in sores or infection. The immobolizing material or cast applied on top of this padding is usually made of plaster of paris or polyurethane-coated fiberglass. The open structure of the immobilizing material outer layers, however, will allow some water to pass through and be absorbed into the traditional padding materials underneath. If the padding becomes wet, it would take many hours to dry, if not days. In addition, skin maceration could occur which can lead to infection by bacteria or fungi. The probability for these types of complications is much greater in pediatric, geriatric, and circulatory impaired patients where the patient is unable to convey their symptoms which results in delayed and prolonged treatment. Furthermore, it is important for the padding to stay dry and have enough "fluffiness" or loft to allow the moisture vapors that are created from perspiration or other sources to be transmitted outwards through the padding.

Some cast padding manufacturers advise the wearer to dry the padding with a hair dryer, should it become wet, to try and avoid these skin related problems. Drying can take several hours and patient compliance is difficult to achieve. Since casts are usually worn for periods ranging from a few weeks up to several months, the wearer is constantly faced with the challenge of maintaining their personal shower or bath routine without getting their cast wet. Some wearers resort to wrapping their limb in a plastic bag so they can take a shower. This approach is cumbersome and doesn't always work that well due to leakage of the seal area. All padding used in conventional casting procedures is "breathable" to a certain extent. "Breathable" can be defined as padding's ability to allow air and/or moisture vapor from body perspiration to pass through it. When water is added to conventional padding on the market today, it tends to compress or "wad up". Moreover, water saturated padding will not allow for effective transfer of moisture away from the skin and will lead to skin maceration if the wet padding is worn for extended periods of time.

Prior art approaches to "breathable", self-drying padding for casting applications include U.S. Pat. No. 5,277,954 which discloses "an adhesive-backed layered composite of padding between two layers of water impermeable, moisture-vapor-permeable film, preferably porous, expanded polytetrafluoroethylene". This product does not allow water to pass through it, but is designed to allow for moisture vapor transmission only. U.S. Pat. No. 5,016,622 discloses an "inner liquid water impermeable, water vapor permeable protective sleeve next to the skin" over which regular types of cast padding can be placed". This two step approach is intended to perform the same basic function as U.S. Pat. No. 5,277,954, except that the product does not have a unitized construction. U.S. Pat. No. 5,380,260 discloses "a moisture vapor permeable, water impervious padding including sheets or strips of lofted non-woven fabric having wax, silicone resin or fluorinated polymer at a surface layer thereof". Finally, U.S. Pat. No. 5,720,714 discloses "a first moisture vapor permeable film layer and a second moisture vapor permeable film layer with air bubbles spaced in between".

The use of cast paddings having a "water impermeable, moisture-vapor-permeable film", as indicated in the four preceding patents, can result in a squishy or water logged feeling against the skin, immediately after the cast is immersed in water. The inherent properties of the moisture vapor permeable films utilized in these designs tend to "trap" any water against the skin until it can be vaporized by normal body temperature. The "water logged" sensation associated with these water impermeable barriers can continue for 45 minutes and beyond, until body heat begins to vaporize the trapped water between the barrier and the skin. The padding systems of the prior art rely on water impermeable and moisture permeable films to achieve their end effect, and do not maximize water runoff underneath the cast or brace.

It is therefore an object of the present invention to provide a water permeable padding design that channels water away from a cast or other immobolizing device.

It is a further object of the present invention to provide a padding for a cast that can be flushed with various solutions for cleansing of the limb beneath while avoiding the accumulation of excess moisture.

It is a further object of the present invention to provide a padding in combination with an orthopedic cast material that can be immersed in water then dried quickly in the open air.

It is a further object of the present invention to provide a padding in combination with an orthopedic cast material with quick drying features as well as improved skin comfort immediately after getting the cast wet.

It is a further object of the present invention to provide a cast that allows for effective transfer of moisture away from the skin thereby avoiding skin maceration.

SUMMARY OF THE INVENTION

The foregoing and other problems are overcome, and other advantages are realized, in accordance with the disclosed, alternative embodiments of these teachings.

A flexible, breathable, water permeable padding utilized in immobilization devices including orthopedic casts or braces is provided. The padding and immobilization device combination incorporates both materials and construction to allow for quick water evacuation, ventilation, and access to the area being immobilized. The padding incorporates a water channeling design which evacuates water while providing open air space around the limb to allow normal body heat to vaporize moisture on the skin. The padding can be applied to any type of synthetic cast or brace or other immobilizing device where water exposure can occur. It allows the synthetic cast or brace wearer the freedom to bathe, shower or swim without any special protective precautions that are currently necessary with traditional padding materials. The padding may be utilized in any immobilization application, even if water exposure is not expected or considered desirable, simply to take advantage of its open, breathable design. Furthermore, this type of immobilization apparatus functions as a skin care and cleansing system to allow a wearer to periodically flush the padding with solutions to stop or inhibit the growth of bacteria and to cleanse the area beneath the padding. Accelerated drying of remaining moisture within the immobilization device can be achieved by using a special external dryer, similar to a hair dryer, or a special attachment which is designed to attach to a regular hair dryer, to blow heated air into the exposed edges of the padding. The efficient circulation of heated air within the padding is made possible by the open internal structural design of the padding itself, which acts in a similar manner to a hot air ducting system.

BRIEF DESCRIPTION OF THE DRAWINGS

The foregoing aspects and other features of the present invention are explained in the following description, taken in connection with the accompanying drawings, wherein:

FIG. 1 illustrates an immobilization apparatus in the form of an arm cast.

FIG. 2 illustrates a padding cross-section of subject invention utilizing notches for increased water evacuation.

FIG. 3 illustrates an alternative padding design for use in subject invention.

FIG. 4 illustrates a flat pre-cut padding configuration with dimensions for use in an arm cast.

FIG. 5 illustrates a tubular configuration of the padding of subject invention.

FIG. 6 illustrates an alternative tubular configuration of the padding of subject invention.

DETAILED DESCRIPTION OF THE PREFERRED EMBODIMENT

Figure 7:
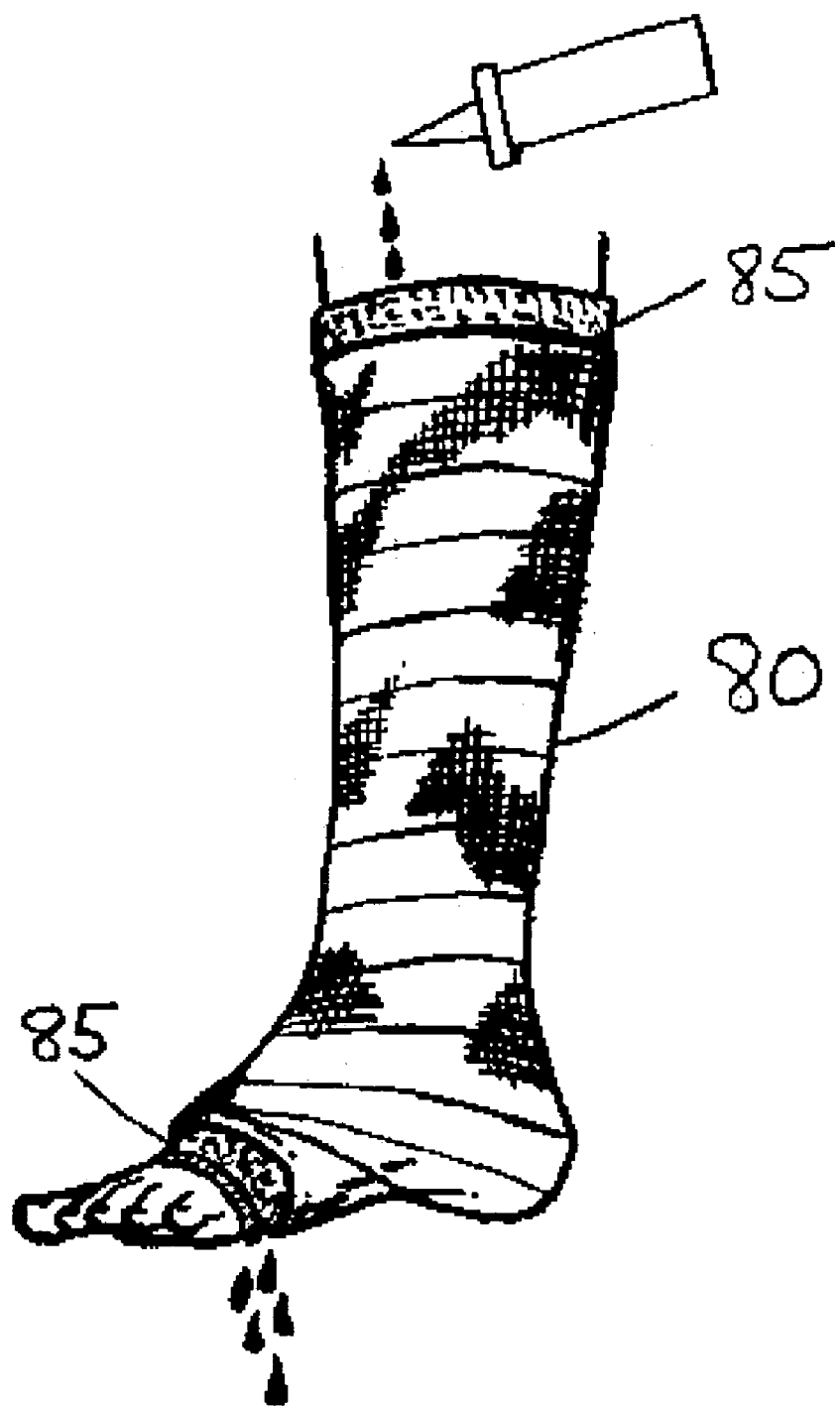
FIG. 7 illustrates a leg cast of subject invention being treated with a skin cleaning and/or moisturizing solution.

FIG. 1 depicts an immobilization apparatus in the form of an arm cast 1 comprising a padding composite 2 overlaid with bandage 3 made of plaster of paris or resin impregnated (synthetic). The bandage 3, after a sufficient passage of time, subsequently hardens to form a rigid cast 1. In one embodiment, the bandage 3 is wrapped around the padding composite 2, while exposing up to about a 1 inch segment 4 of the composite 2. It is important that the padding extend as much as 1" from the edges of the cast or other immobilizing material. Within a few minutes, most of the water is expelled by gravity. The bottom ½" or so of the padding tends to collect some water within it's open internal structure, which can be easily patted dry with a towel to remove the excess water and accelerate the drying process. In addition, the padding extension serves to protect the body part from abrading against the edge of the cast or other immobilizing material.

Referring to FIG. 2, a padding 25 cross-section is disclosed. The padding 25 comprises a gelatinous elastomer or gelatinous viscoelastomer which has hollow compressible columns 30 to provide cushioning and which conforms to the surface area of which it is attached. In an orthopaedic casting application, the padding can have an overall single layer thickness of up to ½ inch.

Padding 25 further comprises water-channeling notches 20 distributed within compressible columns 30. FIG. 2 illustrates the notches being at the bottom 30A and top 30B of compressible columns 30, however, it is understood that the notches 20 may be distributed randomly throughout columns 30 to provide maximum water evacuation through padding 25. If desired, a single cover layer of permeable stretchable stockinet 35 may be attached on either side of padding 25. In one embodiment, to enhance comfort, a single cover layer of permeable stretchable stockinet 35, can be attached to the side of padding 25 that's placed against a patient's skin. Stockinet 35 ranges from relatively open weaves, with as much as 85% of the surface open, to relatively tight weaves, with only about 10% of the surface open. Despite the broad range of these surface properties, they all can promote the fast drying feature due to the various amounts of capillary action which occurs between the interstices of each fabric design.

The padding 25 may also be treated with anti-microbial material to minimize the possibility of bacterial growth within the rigid cast 1. The padding 25 can be produced in a variety of three dimensional open column designs (diamond, square, round, etc) and a variety of heights, wall thicknesses and column widths depending on the final padding properties desired. U.S. Pat. No. 5,749,111 to Pearce, Tony M, incorporated herein by reference for all it discloses, can be utilized as a base material for incorporation of the changes herein described. FIG. 3 depicts an alternative embodiment padding 40 which can be utilized by subject invention. This padding 40 comprises a highly breathable, multi-layer fabric that can be engineered in a variety of thicknesses, densities, compressions, air permeabilities, and softnesses. These types of paddings are known in the art with examples produced by Tytex, Inc, Woonsocket, R.I., USA and Gehring Textiles, Garden City, N.Y. USA. FIG. 3 depicts such a padding 40 cross section comprised of a top layer 45, middle layer 50, and bottom layer 55. Connecting yarns 50 form a soft cushion in connecting top layer 45 and bottom layer 50 to form a unitized type of construction. The height, density and thickness of these yarns can be changed to achieve different cushioning, softness, stretch, water permeability, and air permeability characteristics. These fabrics, also called "spacer fabrics", can be constructed in almost limitless patterns using a wide variety of fibers, including Nomex®, Kevlar®, PBI®, monofilament, spandex and other state-of-the-art yarns. The yarns used, along with the machine set-up also impacts the size and number of openings on the top layer 45 and bottom layer 55 of the unitized construction. The top 45 and bottom 55 layers of the padding can be formed in a variety of surface designs having a relatively smooth cloth-like look or could contain larger openings or "holes" depending on the layer properties that are desired. It is possible to use a smooth layer against the skin and a more open layer against the cast side or vice-versa. It may also be possible to utilize a middle layer having only one side covered which would be placed against the patient's skin. This padding 40 can also be treated with anti-microbial material to minimize the possibility of bacterial growth. Different treatments such as anti-mildew may also be applied in the form of a micro-encapsulated substance. These treatments can be made either on the individual yarn components 50 or after they are converted into a composite structure 40. Furthermore, the padding material, either all or in part, may be treated with a waterproofing material to reduce water absorption within the padding materials.

It is understood that the padding materials and construction designs disclosed may be replaced by anyone of infinite equivalent alternatives that will provide the following padding functions. The first function is to enable the middle of the padding to act like a large open cavity or reservoir of airspace. This provides for rapid collection and runoff of water after the cast is removed from water and allows for quick moisture vapor dispersion for the water that remains against the patient's skin. The second function is to use the same middle layer to provide for the proper amount of cushioning between the limb and outer layers of the cast. The third function is that the materials used have enough conformability to contour to the limb that it is being applied to.

The amount of open internal airspace contained between the top and bottom layers of the padding structure allows for rapid runoff of water through the padding. It is, therefore, important to try to maximize the amount of open internal airspace by volume while still retaining the cushioning properties necessary for the padding use. The amount of open internal airspace space (by volume) for the padding of FIG. 2 calculates to be about 60% while the amount of open airspace for the padding design of FIG. 3 can range from about 20% to about 95% depending on the construction design chosen. The open internal airspace acts much like an air duct to first channel the water away and then to allow for quick dispersal of the moisture vapor which is created from normal body temperatures.

In summary, the most important padding functions are: to create the maximum amount of internal open area for quick water removal and, at the same time, provide enough structure for acceptable cushioning as well as comfort and conformability on the body area being treated. There are other material alternatives that can be adapted to provide the same end result as the sample padding constructions depicted in FIG. 2 and FIG. 3. The materials and constructions described above are not the only approaches that can be taken to achieve these properties. A variety of padding materials which can be used in the present invention to achieve the desired quick drying effect can include, but not be limited to, polyester, nylon, polypropylene, polyurethane, cotton and other natural fibers, rubber, synthetic rubber (non latex), gels, plastics, fiberglass and other petroleum based materials that could be produced in stretchable configurations.

When choosing a padding material for use in the present invention, a number of factors are considered. First, the padding must not unduly absorb and retain water so as to minimize water entrapment within the cast structure. Second, the padding materials must be able to be transformed into a three dimensional configuration where internal air spaces can be formed to rapidly channel the water away by means of gravity. Thirdly, the materials used must possess a degree of elasticity so that they can conform to the limb or body area receiving treatment. Fourth, the materials must be able to be configured in a way so as to provide adequate cushioning of the limb or body part being treated. Other desirable characteristics include lightweight and ease of application.

While the present invention can consist of a wide variety of padding designs, it can also be supplied to the practitioner in a number of product configurations, each requiring its own specific application technique. Without intending to limit the number of possible product configurations, following are several examples that depict the wide variety of ways the subject padding can be presented to the practitioner.

The padding could be produced in a pre-cut flat single use format. It could be supplied in a simple rectangular shape or it can be die cut to more closely fit the anatomy that it would be used on. FIG. 4 depicts a "butterfly"-type padding 60 for a short arm cast, being narrow in the wrist area and wider in the forearm and palm area. Fastening tabs 65 enable the flat sheet of padding 60 to be wrapped around the patient's limb and fastened back onto itself. Fastening tabs 65 can be separate pieces or one continuous strip which are adhered by means of various techniques including but not limited to double and single faced adhesive tape, hook and loop, hook only, adhesive spray or any combination thereof. These closure means can be pre-applied to the padding by the manufacturer or afterwards by the practitioner before placing the padding on the patient. Any brand of synthetic or plaster casting tape could then be applied, in the normal manner, over the padding as herein described.

The padding can be produced in a tubular or conventional flat padding roll format with an adhesive coating on one side to facilitate adhesion of the padding layers to the rigid cast 1. It is also possible to pre-fabricate padding sleeves in various sizes that would fit the anatomy of the limb being covered. The padding can also produced in various durometers depending on the elasticity requirements for the immobilization application.

Referring to FIG. 5, a tubular padding 70 can be formed in a seamless manner, with a circular knitting machine, or with a seam produced by sewing, spray adhesive, heat sealing, double and single faced tape or any other method known in the art. The padding 70 can be provided in a pre-cut, single use format as seen in FIG. 5 or have anatomically proportioned dimensions as illustrated in the padding 75 of FIG. 6. Alternatively, the padding can be supplied in a large multi-use roll, similar to the way most stockinet is sold.

The method of applying a cast utilizing the materials herein described would be initiated by first applying the padding around the affected extremity. This is done in one example by pulling tubular padding 70 or 75 over the extremity being treated then applying any brand of synthetic or plaster casting tape over the padding. In another example, in an application of a body cast or extremity cast utilizing a rolled padding material, the padding would be cut by the practitioner, placed over the area being treated, and fastened back onto itself by any fastening means as previously described. Any brand of synthetic or plaster casting type could then be applied, in the normal manner, over the padding.

It is not unusual for the body part being treated to be immobilized for a few weeks and lasting up to several months in some cases. During this period, bacteria can grow on the skin from exposure to dust, dirt, body perspiration and other environmental influences which can cause foul smelling odors to emanate from the immobilized area. The open internal design of the immobilizing apparatus of subject invention, allows the wearer to periodically flush the cast with a cleansing or disinfecting solution to kill, inhibit or control the growth of bacteria. Furthermore, the wearer is able to flush the immobilizing apparatus with a moisturizing solution to treat dry skin. FIG. 7, illustrates a leg cast comprised of several layers of a urethane impregnated (synthetic) casting material 80 placed over a padding 85 which extends from the top and bottom edge of the cast by about a ½ inch to about an inch. A cleaning/moisturizing and/or disinfecting solution is poured into and around the exposed padding 85 at the top end of the cast, with the solution running out of the exposed padding 85 at the bottom of the cast.

Figure 8:
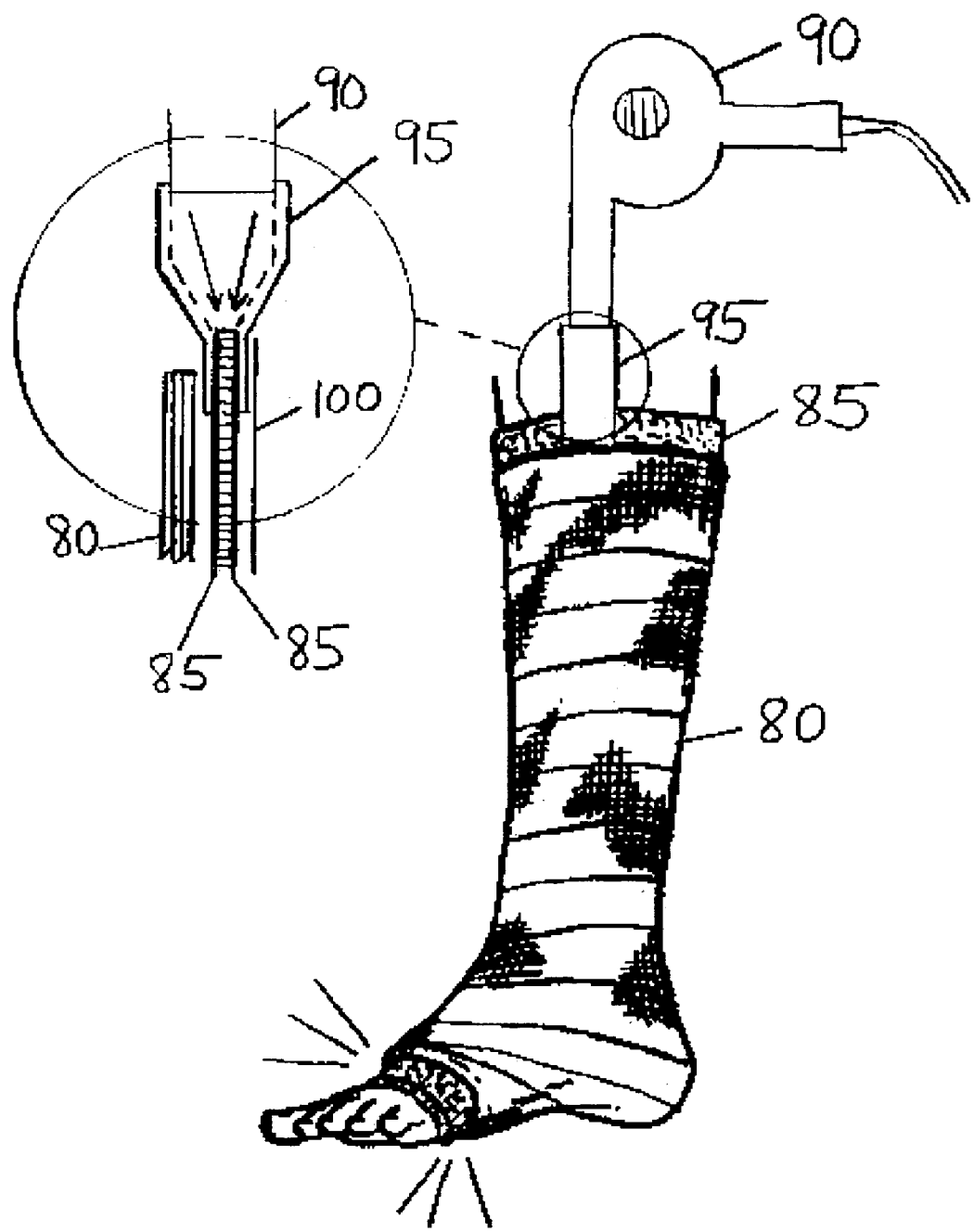
FIG. 8 illustrates a leg cast of subject invention being dried with a hair dryer.

The open internal design of the subject invention further provides a pathway for hot air to be injected into the immobilization apparatus to accelerate drying after the padding becomes wet. FIG. 8 depicts an identical cast structure as illustrated in FIG. 7. Hot air from a hair dryer 90 is injected into the top of the leg cast padding between padding 85 and casting material 80 and exits from the bottom of the cast. A standard hair dryer can be used at a low setting or a special fitting 95 can be added to the hair dryer to better focus the air flow through the cast and to shield the skin from getting too hot from the dryer. A cross section of the fitting 95 within the cast illustrates fitting 95 inserted between cast layer 80 and the outer surface of padding 85 and between the patient's skin 100 and the inner surface of padding 85.

It is understood that the present invention might be embodied in many alternate forms of embodiments where structural support of an article is required and further where the supported article may be exposed to the elements and require quick drying etc. Accordingly, the present invention is intended to embrace all such alternatives, modifications and variances.

While certain embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. An immobilizing apparatus used as an orthopedic cast, brace or splint adapted to immobilize human or animal body parts, comprising:
    an inner protective padding, said padding having a middle layer, a top layer, and a bottom layer, said bottom layer adjacent to the skin, said middle layer comprising a plurality of substantially parallel elongate connecting members, said members having a top and a bottom, said top and said bottom of said connecting members intertwined into said top layer and said bottom layer, said top and said bottom of said connecting members substantially perpendicular to said top and said bottom layer, said connecting members spaced apart from each other creating a plurality of open spaces within said middle layer, said top layer and said bottom layer held in a substantially parallel fixed relation to each other by said elongate connecting members, said top layer, said bottom layer and said middle layer being water permeable, said plurality of open spaces allowing for rapid evacuation of water, moisture and air therethrough, said padding conforming to the surface area to which it is attached, said plurality of open spaces of said middle layer permitting substantial ventilation to said top layer and said bottom layer;
    and an outer immobilizing material layer positioned over said padding top layer.

2. An immobilizing apparatus used as an orthopedic cast, brace or splint adapted to immobilize human or animal body parts as in claim 1, wherein said plurality of members further comprise an anti-microbial material thereon to inhibit or restrict the growth of bacteria in the padding.

3. An immobilizing apparatus used as an orthopedic cast, brace or splint adapted to immobilize human or animal body parts as in claim 1, wherein said plurality of members further comprise an anti-mildew material thereon.

4. An immobilizing apparatus used as an orthopedic cast, brace or splint adapted to immobilize human or animal body parts as in claim 1, wherein the padding has a tubular dimension.

5. An immobilizing apparatus used as an orthopedic cast, brace or splint adapted to immobilize human or animal body parts as in claim 4, wherein said tubular padding comprises anatomically proportioned dimensions.

6. An immobilizing apparatus used as an orthopedic cast, brace or splint adapted to immobilize human or animal body parts as in claim 1, wherein the padding is pre-cut to the dimensions of said surface area to which it is attached.

7. An immobilizing apparatus used as an orthopedic cast, brace or splint adapted to immobilize human or animal body parts as in claim 1, wherein said inner protective padding is exposed about 1 inch from the ends of said immobilizing material layer.

8. An immobilizing apparatus used as an orthopedic cast, brace or splint adapted to immobilize human or animal body parts of claim 1, wherein said top layer and said bottom layer of said padding further comprises a plurality of open spaces.

9. An immobilizing apparatus used as an orthopedic cast, brace or splint adapted to immobilize human or animal body parts as in claim 8, wherein said plurality of open spaces of said top layer and said bottom layer can be changed to create various water permeability characteristics through said top layer and said bottom layer.

10. An immobilizing apparatus used as an orthopedic cast, brace or splint adapted to immobilize human or animal body parts as in claim 9, wherein said top layer and said bottom layer have different water permeability characteristics.

11. An immobilizing apparatus used as an orthopedic cast, brace or splint adapted to immobilize human or animal body parts as in claim 1, wherein said padding comprises one or more of the materials selected from the group consisting of polyester, polypropylene, polyurethane, nylon, cotton, natural fibers, rubber, spandex, lycra, synthetic rubber (non latex), plastics, fiberglass and petroleum based materials that can be produced in stretchable configurations.

12. An immobilizing apparatus used as an orthopedic cast, brace or splint adapted to immobilize human or animal body parts, comprising a padding as in claim 1, and an immobilizing material layer selected from the group consisting of orthopedic casting tapes, braces, or splints.

13. An immobilizing apparatus used as an orthopedic cast, brace or splint adapted to immobilize human or animal body parts as in claim 1, wherein said top, middle, and bottom layers comprise hydrophobic fibers.

14. An immobilizing apparatus used as an orthopedic cast, brace or splint adapted to immobilize human or animal body parts as in claim 1, wherein said top, middle, and bottom layers comprise hydrophilic fibers.

15. An immobilizing apparatus used as an orthopedic cast, brace or splint adapted to immobilize human or animal body parts as in claim 1, wherein said top, middle, and bottom layers comprise a combination of hydrophilic fibers and hydrophobic fibers.

16. An immobilizing apparatus used as an orthopedic cast, brace or splint adapted to immobilize human or animal body parts as in claim 1 wherein said middle layer of said padding includes from about 20 percent to about 95 percent of volume of said open spaces therein.

17. An immobilizing apparatus used as an orthopedic cast, brace or splint adapted to immobilize human or animal body parts as in claim 1, having a total thickness of between about 1/16 inch to about 1/2 inch, said padding positioned between said skin and said immobilizing material.

18. An immobilizing apparatus used as an orthopedic cast, brace or splint adapted to immobilize human or animal body parts as in claim 1, wherein one or more of said plurality of said elongate members are waterproofed.

19. An immobilizing apparatus used as an orthopedic cast, brace or splint adapted to immobilize human or animal body parts as in claim 1, wherein the density distribution of said connecting members of said middle layer can be changed to create various water permeability characteristics throughout said middle layer.

20. An immobilizing apparatus used as an orthopedic cast, brace or splint adapted to immobilize human or animal body parts as in claim 19, wherein said changed density distribution defines channels of open space within said middle layer.

21. An immobilizing apparatus used as an orthopedic cast, brace or splint adapted to immobilize human or animal body parts as in claim 1, wherein said rapid evacuation of water, moisture and air, allows for said padding to substantially dry within 150 minutes of full immersion under water.

22. An immobilizing apparatus used as an orthopedic cast, brace or splint adapted to immobilize human or animal body parts as in claim 1, wherein said inner protective padding is stretchable, said stretchable padding capable of conforming to said surface area in a single layer without folding over onto itself.

23. An immobilizing apparatus used as an orthopedic cast, brace or splint adapted to immobilize human or animal body parts as in claim 1, wherein said outer immobilizing material layer is selected from the group consisting of orthopedic casting tapes, braces, and splinting materials.

24. A method for making an immobilizing apparatus used as an orthopedic cast, brace or splint adapted to immobilize human or animal body parts, comprising:

selecting a padding format to fit the affected extremity, said padding having a middle layer, a top layer, and a bottom layer, said bottom layer adjacent to the skin, said middle layer comprising a plurality of substantially parallel elongate connecting members, said members having a top and a bottom, said top and said bottom of said connecting members intertwined into said top layer and said bottom layer, said top and said bottom of said connecting members substantially perpendicular to said top and said bottom layer, said connecting members spaced apart from each other creating a plurality of open spaces within said middle layer, said top layer and said bottom layer held in a substantially parallel fixed relation to each other by said elongate connecting members, said top layer, said bottom layer and said middle layer being water permeable, said plurality of open spaces allowing for rapid evacuation of water, moisture and air therethrough, said padding conforming to the surface area to which it is attached, said plurality of open spaces of said middle layer permitting substantial ventilation to said top layer and said bottom layer;

applying said padding to the affected extremity; and applying an outer immobilizing material layer over said padding.

25. A method for making an immobilizing apparatus used as an orthopedic cast, brace or splint adapted to immobilize human or animal body parts, as in claim 24, wherein said selected padding formats are selected from the group consisting of tubes, flat sheets, and rolls.

26. A method for making an immobilizing apparatus used as an orthopedic cast, brace or splint adapted to immobilize human or animal body parts, as in claim 24 wherein said selected padding formats are precut.

27. A method for making an immobilizing apparatus used as an orthopedic cast, brace or splint adapted to immobilize human or animal body parts, as in claim 24 wherein said applying step further includes the step of fastening said padding onto itself by fastening means selected from the group consisting of adhesive tapes, adhesive sprays, hooks, and hook and loop.

\* \* \* \* \*